US008664464B2

(12) United States Patent
Munro et al.

(10) Patent No.: US 8,664,464 B2
(45) Date of Patent: Mar. 4, 2014

(54) ABSORBENT MULTILAYER HYDROGEL WOUND DRESSINGS

(75) Inventors: Hugh S. Munro, Chipping Campden (GB); Derek Silcock, Skipton (GB); Simon W. Bayliff, Skipton (GB); Richard Hoskins, York (GB); Susana S. Garcia, Wantage (GB); Helen Burgess, John Towle Close (GB); Justin Barnes, Malmsborough (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 70 days.

(21) Appl. No.: 10/538,427

(22) PCT Filed: Dec. 12, 2003

(86) PCT No.: PCT/GB03/05460
§ 371 (c)(1),
(2), (4) Date: Apr. 4, 2006

(87) PCT Pub. No.: WO2004/052414
PCT Pub. Date: Jun. 24, 2004

(65) Prior Publication Data
US 2006/0200063 A1    Sep. 7, 2006

(30) Foreign Application Priority Data
Dec. 12, 2002 (GB) .................................. 0229024.5

(51) Int. Cl.
| A61F 13/00 | (2006.01) |
| A61K 9/70  | (2006.01) |
| A61L 15/00 | (2006.01) |
| A61L 15/16 | (2006.01) |
| A61F 13/02 | (2006.01) |
| A61F 15/00 | (2006.01) |
| A61F 13/15 | (2006.01) |
| A61F 13/20 | (2006.01) |

(52) U.S. Cl.
USPC ............. 602/46; 424/443; 424/445; 424/446; 424/447; 424/448; 602/41; 602/42; 602/43; 602/47; 602/52; 602/53; 602/54; 602/55; 602/56; 604/304; 604/307; 604/367; 604/368

(58) Field of Classification Search
USPC ............. 602/41–59; 604/304, 307, 368, 387; 424/443, 445–448
See application file for complete search history.

(56) References Cited

U.S. PATENT DOCUMENTS

| 4,541,426 | A  | * | 9/1985  | Webster ........................... 602/47 |
| 5,733,570 | A  | * | 3/1998  | Chen et al. ..................... 424/445 |
| 5,750,585 | A  | * | 5/1998  | Park et al. ....................... 521/143 |
| 5,811,116 | A  | * | 9/1998  | Gilman et al. ................. 424/443 |
| 5,972,452 | A  | * | 10/1999 | Takahashi et al. ............ 428/40.1 |
| 6,136,873 | A  | * | 10/2000 | Hahnle et al. ................... 521/62 |
| 6,174,929 | B1 | * | 1/2001  | Hahnle et al. ................... 521/64 |
| 6,191,335 | B1 |   | 2/2001  | Robinson |
| 6,566,575 | B1 | * | 5/2003  | Stickels et al. ................. 602/41 |
| 6,600,085 | B2 | * | 7/2003  | Sun et al. ........................ 602/56 |
| 7,164,054 | B2 | * | 1/2007  | Mori et al. ...................... 602/57 |
| 2003/0153860 | A1 | * | 8/2003 | Nielsen et al. ................. 602/43 |
| 2003/0176827 | A1 | * | 9/2003 | Chandra et al. ................ 602/48 |
| 2005/0256437 | A1 | * | 11/2005 | Silcock et al. ................. 602/48 |

* cited by examiner

*Primary Examiner* — Patricia Bianco
*Assistant Examiner* — Brandon L Jackson
(74) *Attorney, Agent, or Firm* — Brian B. Shaw, Esq.; Paul A. Leipold, Esq.; Harter Secrest & Emery LLP

(57) ABSTRACT

The invention provides wound dressings comprising an absorbent (porous) hydrogel composition comprising a foam portion which comprises a flexible plasticized hydrophilic polymer matrix having an internal cellular structure, and a continuous portion which comprises a flexible plasticized hydrophilic polymer matrix having relatively continuous internal structure. The continuous portion of the hydrogel composition includes apertures providing fluid flow communication through the continuous portion between an external surface of the continuous portion and the foam portion whereby the foam portion can take up external water or other fluid into the cellular structure through the apertures of the continuous portion. The continuous portion of the hydrogel composition may be tacky to the skin, allowing its use as a bioadhesive.

25 Claims, No Drawings

ABSORBENT MULTILAYER HYDROGEL WOUND DRESSINGS

CROSS-REFERENCE TO RELATED APPLICATIONS

This application is a National Stage application under 35 U.S.C. 371 of PCT/GB03/05460, filed 12 Dec. 2003, which claims priority from GB0229024.5 filed Dec. 12, 2002.

FIELD OF THE INVENTION

The present invention relates to wound dressings comprising absorbent (porous) hydrogel compositions, in particular for applications where a relatively high speed of fluid uptake is required.

The expressions "hydrogel" and "hydrogel compositions" used herein are not to be considered as limited to gels which contain water, but extend generally to all hydrophilic gels and gel compositions, including those containing organic non-polymeric components in the absence of water.

BACKGROUND OF THE INVENTION

U.S. Pat. No. 5,750,585 (Park et al), the disclosure of which is incorporated herein by reference, describes certain superabsorbent hydrogel foams comprising a solid phase and a gas phase, in which the volume of the gas phase exceeds the volume of the solid phase. Such foams may generally be thought of as relatively light foams. The preferred density of the foams is stated to be between 0.015 and 0.5. Higher densities are stated to be undesirable as the swelling of the foam is slower (prior art, column 7, lines 35 to 46).

The prior art foams are stated to have potential utility as superabsorbents, oral drug delivery vehicles and gastric retention devices for diet control.

Hydrogel foams of polyacrylamide, polyvinylpyrrolidone, poly-(2-hydroxyethyl-methacrylate) or poly-(2-hydroxypropyl-methacrylate) are specifically mentioned.

The particular foams described in the said prior art document do not contain any organic plasticiser and are dried to provide superabsorbency. They are generally formed by polymerising at least one suitable hydrophilic olefin monomer compound in an aqueous solution containing a surfactant and about 0.1 to about 10% by weight of a crosslinking agent having at least two alkenyl groups; introducing gas into the monomer solution during the polymerisation step to form the foamed polymer matrix; and drying the foam.

The Examples of the said prior art patent show the use of sodium bicarbonate as a carbon dioxide blowing agent to generate the gas, although the general description mentions also mechanical introduction of gas into the monomer solution. The introduction of gas into the monomer solution during the polymerisation step is inconvenient, and would generally limit the polymerisation procedure to small batchwise production.

The foams described in U.S. Pat. No. 5,750,585 swell slowly on contact with water, typically over a time period of about 1 to 3 hours (see the Figures in the prior art patent). This slowness of water uptake makes the foams unsuitable for use in the applications contemplated in the present invention. The relatively low density of the foam makes it unsuitable for forming into films and sheets having acceptable mechanical strength.

U.S. Pat. No. 6,136,873 (Hahnle et al), the disclosure of which is incorporated herein by reference, describes certain superabsorbent hydrogel foams. The preferred density of the foam is stated generally to be between 0.05 and 0.7 g/cm$^3$.

The prior art foams are stated to have potential utility as superabsorbents in diapers, sanitary towels and incontinence articles, and in certain other conventional uses for superabsorbents. Dressing material for covering wounds is mentioned as one potential application (column 15, lines 24 to 26).

The prior art document contains extensive lists of possible monomers and monomer mixtures for use in the polymerisable mixture. However, all the examples use a mixture of acrylic acid and sodium acrylate.

The particular foams described in the said prior art document may contain certain plasticisers and are stated to be usually dried after polymerisation, preferably to a water content of between 15 to 35% by weight.

The gas introduced into the monomer mixture is stated to be "fine bubbles of a gas inert to free radicals". Examples show the use of mechanical stirring under an atmosphere of argon or carbon dioxide.

The foams described in U.S. Pat. No. 6,136,873 swell on contact with water, the absorption speed being reported as the parameter AS in the Examples. As used therein, AS=20/t, where t=the time for a 1 g piece of the foam to absorb 20 g of water (i.e. a 2000% uptake). While the water uptake rate appears to be faster than the foams reported in U.S. Pat. No. 5,750,585, the manufacturing process is inconvenient in view of the need for an inert gas atmosphere, and is most suitable only for batchwise production.

A large amount of research has been conducted into unfoamed, relatively non-porous, hydrogels based on hydrophilic polymers, e.g. for use as skin adhesives for a range of applications in skin-adhesive articles. Such materials exhibit a range of properties which make them suitable for skin adhesives. Representative references include PCT Patent Applications Nos. WO-97/24149, WO-97/34947, WO-00/06214, WO-00/06215, WO-00/07638, WO-00/46319, WO-00/65143 and WO-01/96422, the disclosures of which are incorporated herein by reference.

BRIEF DESCRIPTION OF THE INVENTION

The present invention is based on our surprising finding that porous hydrogels can be made in a convenient manner with very acceptable water uptake speeds. The manufacturing process, particularly at the polymerisation stage, can be batchwise, partially continuous or continuous. The porous hydrogels can be prepared in sheet or layer form. The porous hydrogels are characterised by portions which have an internal cellular (e.g. foam) structure and portions which are relatively continuous (i.e. have a relatively non-cellular internal structure). The relatively continuous portions have apertures provided therethrough, to assist uptake of water and other fluids to the porous portion through the continuous portion. The porous hydrogels can combine the requirements of good gel flexibility, good mechanical strength and good fluid absorption capacity, optionally also with tackiness to the skin.

The expressions "comonomer", "monomer" and like expressions used herein include ionic and non-ionic monomers and monomer mixtures. Correspondingly, the expressions "polymerize", "polymers" and like expressions include both homopolymerisation and copolymerisation, and the products thereof.

According to a first aspect of the present invention, there is provided a wound dressing comprising a hydrogel composition, said hydrogel composition comprising a first portion which comprises a flexible plasticised hydrophilic polymer matrix having an internal cellular structure, and a second portion which comprises a flexible plasticised hydrophilic polymer matrix having a relatively continuous internal structure, wherein the said second portion of the hydrogel composition includes apertures providing fluid flow communication through the said second portion between an external surface of the said second portion and the first portion whereby the first portion of the hydrogel composition can take up external water or other fluid into the cellular structure through the apertures of the said second portion.

The hydrogel composition is preferably present in the form of a multi-layer sheet, each portion constituting a layer.

The first portion may comprise a porous foam having an internal cellular structure such that the volume ratio of cell void to matrix is greater than about 1:3, more preferably greater than about 1:1, and the second portion may comprise a relatively non-porous matrix, which may have substantially no cell voids or only occasional cell voids (e.g. a volume ratio of cell void to matrix less than about 1:10, for example less than about 1:20). The said second portion of the hydrogel composition will be referred to herein as "continuous", which expression is used in the relative sense explained above.

The apertures of the second portion of the hydrogel composition may continue into the first portion of the composition and thus invade it to some extent. However, they preferably do not penetrate the first portion of the hydrogel entirely. Such an arrangement limits mechanical weakening of the first portion and prevents absorbed fluids (e.g. wound exudates) leaking through the first portion when the hydrogel is in use.

One or both of the said portions of the hydrogel composition may be tacky to the skin. The hydrogel composition is normally in sheet form. The outward facing surface of the said second portion typically defines a skin-contactable surface of the hydrogel composition, most preferably a bioadhesive skin-contactable surface. Water and body fluids can be taken up into the first portion of the hydrogel composition, via the apertures provided through the second portion. The skin-contactable surface of the hydrogel composition is usually protected prior to use by an overlying release layer.

It is preferred that the said first, relatively porous, portion of the hydrogel composition has a first water uptake rate and the said second, relatively non-porous, portion of the hydrogel composition has a second water uptake rate (disregarding the apertures) which is less than the first. The first water uptake rate may be very fast, e.g. comparable with the rate of absorption of water by absorbent paper kitchen roll. The absorption capacity of the hydrogel composition will generally be at least about 30% by weight (i.e. the weight of water taken up and held at saturation will be at least about 30% of the weight of the hydrogel composition used), and may be as much as about 20000%. More typically, the absorption capacity of the hydrogel composition will be between about 300% and about 10000%. For convenience, the said first portion of the hydrogel composition will be referred to herein as "porous", which expression is used in the relative sense explained above.

A suitable process for the preparation of the porous hydrogel composition used in the first aspect of the invention comprises polymerising a polymerisable mixture comprising a hydrophilic monomer and optionally one or more comonomer, wherein the polymerisable mixture prior to polymerisation comprises a first portion including a relatively high concentration of introduced gas bubbles and a second portion including a relatively low concentration of gas bubbles, and forming the apertures in the second portion of the hydrogel composition simultaneously with, or separately from, formation of the polymer matrix.

The gas bubbles are preferably predominantly or entirely of air, and are preferably introduced into the polymerisable mixture under an atmosphere consisting predominantly or entirely of air.

The said first portion of the polymerisable mixture forms the porous portion of the hydrogel composition after polymerisation, and the said second portion of the polymerisable mixture forms the continuous portion of the hydrogel composition after polymerisation. The first portion of the polymerisable mixture preferably has a bubble to mixture volume ratio greater than about 1:3, more preferably greater than about 1:1, and the second portion of the polymerisable mixture preferably has substantially no bubbles or only occasional bubbles (e.g. a volume ratio of bubbles to mixture less than about 1:10, for example less than about 1:20).

The polymerisation step in the above process is preferably a free radical polymerisation performed in air using a polymerisation inducing device such as a heat, light (e.g. UV light) or other radiation source which is in relative motion with respect to the polymerisable mixture. In this way, a moving line-wise polymerisation procedure can take place, rather than the static batchwise procedures available from the prior art. The polymerisable mixture is preferably laid down in sheet or layer form on a suitable support arrangement for the polymerisation procedure, whereby the first portion of the polymerisable mixture typically sits on the second portion in the manner of a "head" on beer.

The apertures may suitably be formed simultaneously with formation of the polymer matrix. In a preferred embodiment, this is achieved by laying the polymerisable mixture down prior to polymerisation on a support arrangement comprising a surface from which projections extend. The projections correspond in shape and location to the desired configuration and location of the apertures, and preferably extend only part way into the laid down polymerisable mixture, so that they extend into the polymer resulting from the polymerisation to a distance sufficient to establish fluid flow communication apertures through the continuous portion of the hydrogel composition when the hydrogel composition is removed from the upper surface of the support arrangement, but preferably not so far as to entirely penetrate the porous portion of the hydrogel composition.

Most preferably, the support arrangement comprises a structure which underlies and supports a sheet material adapted to receive the laid down polymerisable material, the sheet material being removable from the underlying structure, e.g. after completion of polymerisation, and the said projections extending from the upper surface of the sheet material. The sheet material may have a non-stick surface, so that it may easily be removed from the hydrogel composition after completion of polymerisation. The sheet material is preferably adapted to constitute a release layer for protecting the skin-contactable surface of the polymerised hydrogel composition prior to use. After laying down the polymerisable material on the sheet material, and conducting the polymerisation reaction, the hydrogel composition and the release layer may be used in contact with each other in a subsequent process for manufacturing an article including the hydrogel composition. Alternatively, a further release layer may suitably be applied to the exposed surface of the freshly polymerised hydrogel composition, to protect the same for storage or transportation. At the times of subsequent processing and use, the respective release layer is peeled away and may be discarded.

In the wound dressings according to the present invention preferably at least one face of the hydrogel composition is in contact with a release layer provided with projections which extend into the hydrogel sheet, most preferably only part way into the hydrogel sheet.

A porous hydrogel composition for use in the present invention may generally be prepared by a process which comprises polymerising a polymerisable mixture comprising a hydrophilic monomer selected from monomers and monomer mixtures, wherein the polymerisable mixture includes introduced gas bubbles.

Certain aspects of such a manufacturing process, and the products thereof, are novel and inventive in the context of wound dressings.

Preferably, the process comprises polymerising a polymerisable mixture comprising a hydrophilic monomer and optionally one or more comonomer, wherein during the polymerisation the polymerisable mixture is in contact with a support surface from which projections extend into the polymerisable mixture, and the polymerisable mixture includes introduced gas bubbles.

Preferably, the process comprises polymerising a polymerisable mixture comprising a hydrophilic monomer and optionally one or more comonomer, wherein during the polymerisation the polymerisable mixture is in contact with a support surface from which projections extend into the polymerisable mixture, the polymerisable mixture includes bubbles consisting predominantly or entirely of air, the bubbles having been introduced into the mixture under an atmosphere consisting predominantly or entirely of air, and the mixture is laid down for the said polymerisation on the said support surface after introduction of the bubbles into the polymerisable mixture but before polymerisation.

The polymerisable mixture preferably has a bubble to mixture volume ratio greater than about 1:3, more preferably greater than about 1:1.

The polymerisation step is preferably a free radical polymerisation performed in air using a polymerisation inducing device such as a heat, light (e.g. UV light) or other radiation source which is in relative motion with respect to the polymerisable mixture. In this way, a moving line-wise polymerisation procedure can take place, rather than the static batch-wise procedures available from the prior art. The polymerisable mixture is preferably laid down in sheet or layer form on a suitable support arrangement for the polymerisation procedure.

The procedures of laying down the gassed (foamed) polymerisable mixture preferably comprises casting the gassed mixture into the foam of a relatively thin sheet, e.g. up to about 8 mm thick.

In a second aspect, the present invention provides the use of a hydrogel composition comprising a first portion which comprises a flexible plasticised hydrophilic polymer matrix having an internal cellular structure, and a second portion which comprises a flexible plasticised hydrophilic polymer matrix having relatively continuous internal structure, wherein the said second portion of the hydrogel composition includes apertures providing fluid flow communication through the said second portion between an external surface of the said second portion and the first portion whereby the first portion of the hydrogel composition can take up external water or other fluid into the cellular structure through the apertures of the said second portion, for the preparation of a dressing for the treatment of wounds and burns.

Preferably, the dressing is a wound dressing according to the first aspect of the invention.

Preferred and alternative features and embodiments for the second aspect of the invention are as described above in relation to the first aspect of the invention.

DETAILED DESCRIPTION OF THE INVENTION

The Hydrogel Composition—Internal Structure

The internal cellular structure of the porous hydrogel composition or, when porous and continuous portions are present, the porous portion of the hydrogel composition, may be closed-cell throughout, open-cell throughout, or may have regions of closed-cell structure and regions of open-cell structure. Generally speaking, an open-cell structure will absorb fluid at a faster initial rate than a closed-cell structure, by reason of the interconnection of the internal cells.

Where porous and continuous portions of the hydrogel composition are present, they may suitably comprise layers, which may be of the same or different materials. The layers may be integrally formed or may be laminated together, optionally with intermediate bonding media.

The said porous and continuous portions of such a hydrogel composition are preferably of the same material and integrally formed in a single polymerisation step.

In the polymerisation step, to be described in more detail below, a fluid pre-gel material is preferably gassed with bubbles of a gas, prior to laying down the pre-gel. The gas is preferably air. To prepare a hydrogel composition comprising porous and continuous portions, the lain down pre-gel is then preferably allowed or assisted to partially "drain", by which is meant that a certain amount of the pre-gel material is allowed to revert to an essentially continuous, unfoamed, fluid state to form the second portion of the polymerisable mixture. By controlling the extent of draining, the relative thickness of the porous and continuous portions in the resulting cured hydrogel composition can be controlled. To prepare a porous hydrogel composition without a continuous portion, draining is avoided.

Where the porous and continuous portions of the hydrogel composition are present and are of different materials, the portions may suitably also be integrally formed in a single polymerisation step. We have found that the first (foam) portion of the laid down polymerisable mixture is usually relatively robust, and will not collapse if additional ingredients, e.g. comonomers, are added onto the mixture as a liquid dispersion, solution or mixture before the polymerisation step. In practice, the added ingredients percolate down through the first portion of the mixture and preferentially invade the fluid second portion below. By controlling the time allowed for this process, a range of differential-composition multi-layer porous hydrogels can be prepared conveniently, using a single polymerisation step to produce essentially the final hydrogel, without the need for lamination and handling of individual component layers after polymerisation or for laminar laying down of different polymerisable mixtures.

The Hydrogel Composition—External Form

The hydrogel composition may suitably be present in the form of a sheet having first and second major faces, each of said first and second major faces being in contact with a protective release layer, for example siliconised plastic or paper, at least one of the release layers having any necessary characteristics defined and described herein for the various aspects of the invention. Alternatively, the hydrogel composition may be present in the form of a sheet having first and second major faces, one of said first and second major faces being in contact with a protective release layer, for example siliconised plastic or paper, the release layer having any necessary characteristics defined and described herein for the various aspects of the invention, and the other of said first and second major faces being in contact with a part of a larger article, e.g. a backing member forming part of a wound or burn dressing, a biomedical electrode or another article. Particularly preferred are articles where a bioadhesive hydrogel layer is to be provided in use between the article and the skin of a patient. Such articles are exemplified below (see "Applications"). Still further, the hydrogel composition may be present in the form of a sheet having a woven or non-woven fabric, or a net, embedded therein.

The hydrogel sheets may typically have a substantially uniform thickness, The hydrogel sheets may typically have a thickness in the range of about 0.5 mm to about 10 mm, preferably from about 1 mm to about 5 mm. The hydrogel composition may suitably be in the form of a sheet having a mean basis weight of hydrogel in the range of about 0.1 kg/m$^2$ to about 2.5 kg/m$^2$.

For the preparation of a hydrogel composition in the form of a sheet, the process according to the invention may include initially forming a sheet of the pre-gel, and subsequently carrying out the polymerisation step so that the sheet hydrogel is formed in situ by the polymerisation reaction, as described in more detail below. Most preferably, material is not substantially added to or removed from the resultant hydrogel composition, although in some cases some degree of subsequent conditioning and/or modification may be desirable.

When the hydrogel composition contains water, the water may be present in any suitable amount. The typical range of water content is between 0 and about 95% by weight of the hydrogel. The hydrogel composition may conveniently be classified as "high water content" or "low water content". The expression "high water content" refers particularly to hydrogel compositions comprising more than about 40% by weight of water, more particularly above about 50% by weight, and most preferably between about 60% and about 95% by weight. The expression "low water content" refers particularly to hydrogel compositions comprising up to about 40% by weight of water.

The apertures of the continuous portion of the hydrogel composition are preferably provided in a grid or array across the surface of the hydrogel composition, and spaced far enough apart from each other to effectively restrict granulation (scab formation) between adjacent apertures when in contact with a wound. Typically, the apertures may be between about 0.5 and about 1.5 cm apart, more preferably between about 0.6 and about 1.0 cm apart. The apertures are preferably tapered so that their external ends are somewhat (e.g. between about 20% and about 1000%) wider than their internal ends. In this way, allowing for the inherent flexibility of the polymeric matrix material comprising the continuous portion, the apertures can preferentially permit fluid flow from the wearer's skin to the porous portion of the hydrogel, in comparison to the reverse direction. Fluid flow in the reverse direction would tend to close the internal end of the aperture, obstructing the flow. Such a one-way effect assists in preventing leakage of fluid from the porous portion of the hydrogel, when in use it functions as a fluid reservoir.

The Hydrogel Composition—Physical Parameters

The density of the hydrogel compositions used in the present invention can be selected within a wide range, according to the materials used and the manufacturing conditions. Generally speaking, the bulk density of the total hydrogel composition may be in the range of about 0.05 to about 1.5 g/cm$^3$, more typically in the range of about 0.3 to about 0.8 g/cm$^3$.

The water activity of the hydrogel compositions of the present invention typically lies within the range of 0 to about 0.96, as measured by an AquaLab Series 3TE water activity meter.

The water uptake rate of the hydrogel compositions of the present invention (or, where the composition includes a portion which is more porous than another portion, of the more porous portion) typically lies within the range of at least about 2 µl/s, more preferably between about 2 and about 100 µl/s, as measured by the technique of applying a 5 µl drop of water from a syringe onto the face of the sheet hydrogel and measuring the reduction in volume of the drop over a period of 0.1 s starting from contact between the drop and the hydrogel, and extrapolating to a rate expressed as volume per second, the measurements being made using a Scientific and Medical Products DAT1100 dynamic contact angle analyser. A water uptake rate of, say, 25 µl/s, indicates complete absorption of the applied water in 0.2 s.

The water uptake rate of the hydrogel compositions of the first aspect of the present invention from the continuous portion side is typically less than the rate from the porous portion side, as measured by the same technique.

The absorption capacity of the hydrogel composition will generally be between about 30% and about 20000%. More typically, the absorption capacity of the hydrogel composition will be between about 300% and about 10000%.

Preparative Method—General

The processes for the preparation of porous hydrogels generally comprise polymerising a polymerisable mixture comprising at least one hydrophilic monomer, wherein the polymerisable mixture includes introduced gas bubbles, preferably, but not limited to, air bubbles.

In one embodiment, the polymerisable mixture can comprise a first portion including a relatively high concentration of introduced gas bubbles and a second portion including a relatively low concentration of gas bubbles.

The polymerisation is preferably a free radical polymerisation of a fluid polymerisable mixture comprising (1) a free radically polymerisable hydrophilic monomer, optionally together with at least one free radically polymerisable comonomer; and (2) one or more cross-linking agent comprising a multifunctional unsaturated free radically polymerisable compound;

the polymerisation being conducted in the presence or absence of a plasticiser, with the proviso that when the polymerisation is conducted in the absence of a plasticiser, a plasticiser is added to the polymer product of the polymerisation.

The polymerisable mixture (pre-gel) preferably includes the monomer(s) at a total monomer level of from about 5% to about 70% by weight of the total mixture, more particularly from about 10% to about 60% by weight, most preferably from about 15% to about 50% by weight.

When the polymerisation is conducted in the presence of a plasticiser, one or more different plasticiser and/or more of the same plasticiser may, if desired, be added to the polymer product of the polymerisation.

The plasticiser may be selected from aqueous and non-aqueous systems. Water or a mixture of water and a water-miscible organic plasticiser may suitably be used as an aqueous plasticiser. When a non-aqueous plasticiser is used, it may suitably be an organic plasticiser. Please see below ("Plasticiser"), for more details of plasticiser systems.

Preparation and Laying Down of the Polymerisable Mixture

In preparing hydrogel compositions in accordance with the invention, the ingredients are initially mixed to provide an ungassed polymerisable reaction mixture in the form of an initial fluid pre-gel.

The initial fluid pre-gel is then blown to introduce a gas into the mixture before polymerization. The gas can be introduced by mechanical means or by introduction of a blowing agent.

Mechanical means include the use of a high speed blender or propeller under an atmosphere of the gas, or the introduction of the gas into the liquid through a capillary, nozzle or microporous surface. A blowing agent is any substance or combination of substances capable of producing the gas upon introduction into the mixture and application of any necessary initiation steps. Examples of blowing agents include carbonates or metal powders which react with acidic conditions to generate hydrogen or carbon dioxide, such as sodium bicarbonate, and chemical agents which liberate gas under the influence of heat, such as dipotassium diazomethionate, N-nitroso-β-amino-ketones or sodium borohydride. Initiation of blowing will be achieved in any appropriate way, according to the chemicals being employed. Such initiation procedures will be well within the capacity of those skilled in the art.

The preferred gas for use in the present invention is air, which is preferably introduced into the initial pre-gel by mechanical means. To produce uniform cells in the porous portion of the hydrogel, the air bubbles introduced must be uniformly dispersed and the dispersion substantially maintained up until the point of gelation at polymerization.

The ingredients of the initial pre-gel are preferably mechanically mixed in such a way as to foam the mixture by the mechanical introduction of many small air bubbles. A typical mixing procedure would use a paddle stiffer for up to about 5 minutes at a paddle speed of up to about 800 rpm.

The viscosity of the initial pre-gel may need to be controlled. On the one hand, the viscosity should be low enough to permit effective introduction of the gas, as described below. On the other hand, the viscosity should not be so low that all the introduced gas bubbles rise to the surface and dissipate into the atmosphere before polymerization can take place to form the polymeric matrix. However, as explained above, a certain degree of "draining" is preferred, in order to obtain the hydrogel composition comprising integral porous and continuous portions in one polymerization step. We have found that a viscosity of up to about 100 mPas, more typically less than about 100 mPas, and most preferably lass than about 50 mPas (as measured in a Brookfield Viscometer with a S18 spindle in a closed volume at a speed of 20 rpm) is suitable for the initial pre-gel before introduction of gas, e.g. between about 10 and about 50 mPas.

The viscosity of the pre-gel mixture will rise as a result of this foaming procedure, to a typical range of between about 200 and about 1000 mPas (as measured in a Brookfield Viscometer with a S18 spindle in a closed volume at a speed of 2 rpm).

The gassed pre-gel mixture is then preferably laid down (cast) onto a suitable support arrangement prior to exposure to the source of the polymerising heat or radiation. The upper surface of the support arrangement is preferably provided by the sheet that will constitute the protective release layer to be provided with the hydrogel composition before use of any article in which it is included. Further details of a preferred embodiment of this release layer are given below ("Apparatus").

In the time delay between casting onto the support arrangement and irradiation, the foamed pre-gel mixture may be allowed to "drain", whereby a relatively bubble-free fluid layer forms under the foam layer, as previously described in connection with some aspects of the present invention.

The foam layer is usually mechanically stable enough that at least one further monomer or other desired component or components of the hydrogel composition can be added to the pre-gel mixture as it rests on the support arrangement awaiting polymerisation. Such additional components are typically applied on top of the foam layer in the form of a fluid dispersion, mixture or solution, e.g. in water, which then percolates down through the foam layer and mixes with any relatively bubble-free fluid layer underneath the foam. In this way, the composition of a continuous portion of the final hydrogel composition can be made different from that of the porous layer of the final composition, in a convenient way which still requires only one polymerisation step and can avoid or at least limit the degree of post-polymerisation handling, manufacture and processing of the product that is required.

The polymerisable mixture is then passed to the polymerisation step, which will now be discussed.

The Polymerisation Reaction

Any suitable free radical polymerisation reaction may be used, according to the monomers present in the pre-gel. The range of reactions and their appropriate initiation and other conditions will be well known to those of ordinary skill in this art.

For example, the free radical polymerisation may be initiated in generally known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The pre-gel mixture may include appropriate substances (initiators), at appropriate levels, e.g. up to about 5% by weight, more particularly between about 0.002% and about 2% by weight, which serve to assist the polymerisation and its initiation, in generally known manner.

In one embodiment, the process involves free radical polymerisation and the use of a photoinitiator or a combination of photo- and other initiation. Preferably the reaction mixture comprises an amount of photoinitiator of from about 0.003% to about 0.5%, and particularly from about 0.003% to about 0.4%, most particularly from about 0.009% to about 0.2%, by weight of the total polymerisation reaction mixture. If desired, the low levels of photoinitiator described in WO-01/96422 may be used.

In one preferred embodiment, the polymerisable mixture and the source of the polymerization initiator (e.g. the radiation source) move relative to one another for the polymerization step. In this way, a relatively large amount of polymerisable material can be polymerized in one procedure, more than could be handled in a static system. This moving system is referred to herein as continuous production, and is preferred.

Preferred photoinitiators include any of the following either alone or in combination:

Type I-α-hydroxy-ketones and benzilidimethyl-ketals e.g. Irgacure 651. These are believed on irradiation to form benzoyl radicals that initiate polymerisation. Photoinitiators of this type that are preferred are those that do not carry substituents in the para position of the aromatic ring. Examples include Irgacure 184 and Daracur 1173 as marketed by Ciba Chemicals, as well as combinations thereof.

A particularly preferred photoinitiator is 1-hydroxycyclohexyl phenyl ketone; for example, as marketed under the trade name Irgacure 184 by Ciba Speciality Chemicals. Also preferred are Daracur 1173 (2-hydroxy-2-propyl phenyl ketone) and mixtures of Irgacure 184 and Daracur 1173.

Photo-polymerisation is particularly suitable, and may be achieved using light, optionally together with other initiators, such as heat and/or ionizing radiation. Photoinitiation will usually be applied by subjecting the pre-gel reaction mixture containing an appropriate photoinitiation agent to ultraviolet (UV) light. The incident UV intensity, at a wavelength in the range from 240 to 420 nm, is typically greater than about 10 mW/cm². The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer present, the nature of the monomer(s) present, the presence of dissolved oxygen, the presence of polymerisation inhibitor, the thickness of the reaction mixture when coated onto the substrate and the nature of substrate onto which the reaction mixture is coated.

Apparatus

The apparatus used is generally conventional and commercially available.

As mentioned above, however, the support arrangement on which the gassed polymerisable mixture is laid down preferably supports, and thereby presents as its upper surface, the release layer.

Any necessary apertures may preferably be formed in the hydrogel composition by using a support surface for the polymerisable mixture that comprises projections extending upwardly from the support surface at least part way into the polymerisable mixture. The support surface preferably comprises an upper surface of a release layer supported on an underlying support structure. In the case where the laid down polymerisable mixture drains before polymerisation, the projections preferably extend into the polymerisable mixture to an extent sufficient to establish fluid flow communication apertures through the continuous portion of the hydrogel omposition when the polymerised hydrogel is removed from the support surface, but not so far as to penetrate the porous portion of the hydrogel composition.

The projections preferably taper inwards from their base, whereby the apertures—which will conform to the outer surface of the projections—adopt a corresponding tapered shape.

The projections will suitably be up to about 3 mm in height, and spaced according to the desired spacing of the apertures in the resultant hydrogel.

In one preferred embodiment, the release layer is formed of a plastic sheet material, such as a polyolefin (e.g. polyethylene), the projections being moulded portions of the sheet or formed in the sheet. Such formed projections may conveniently comprise nipples formed by embossing or spiking the plastic sheet with tapered prongs from one side, suitably with at least localised heating of the sheet. The prongs may penetrate the sheet, as it does not matter if a small amount of the polymerisable mixture leaks through any small hole. The plastic material may optionally be coated with a non-stick material such as a silicone.

The support sheet is normally formed from flexible thermoplastic material. Suitable materials include polyesters and polyolefins. Preferably, the hydrogel facing surface of the support sheet is a release surface. That is to say, a surface that is only weakly adherent to the hydrogel to assist peeling of the hydrogel layer from the cover sheet. For example, the cover sheet may be formed from a non-adherent plastic such as a fluoropolymer, or it may be provided with a release coating such as a silicone or fluoropolymer release coating.

In some embodiments, the support sheet is provided with a recess defining a mold for a sheet of hdrogel composition of predetermined shape, the projections in the support sheet extend into the recess, and the hydrogel composition is received in the recess. The recess is typically a shallow recess dimensioned to receive the hydrogel composition and any additional layers such as perforated layers or absorbent layers that are coextensive with the hydrogel composition. Typically the depth of the recess is from 1 to 10 mm, preferably from 2 to 8 mm. The recess may be provided by thermoforming.

The support sheet acts as a mold for the hydrogel, and the projections in the define the shape of apertures in the hydrogel composition. It is a particular advantage of the present invention that this enables the porosity of the hydrogel composition to be controlled accurately. The projections may be square or cylindrical, but preferably the projections in the are tapered, whereby apertures in the hydrogel composition are correspondingly tapered.

Preferably, the projections are substantially in the form of tapered geometric bodies such as truncated cones, pyramids or the like. Preferably, the projections of such tapered projections have a base dimension of from 0.5 mm to 5 mm, and an apical dimension (at the top surface of the hydrogel layer) of from 0.05 to 2 mm. More preferably, the projections have a base dimension as herein defined of from 1 mm to 3 mm, and an apical dimension of from 0.1 to 1 mm. Preferably, the projections have an average angle of taper (measured from the perpendicular to the plane of the support sheet) of from 10 to 60 degrees.

Preferably, the height of the projections is from 0.1 to 5 mm, more preferably from 1 to 3 mm. Preferably, the density of the projections is from 1 to 400 per cm², more preferably from 10 to 100 per cm². Preferably, the mean cross sectional area of the projections at their mid-point (half height) is from 5 to 50% of the total area of the central region of the top sheet, more preferably from 10 to 25% of the said total area. Preferably, the projections are arranged in a regular array. Projections of this type may be manufactured, for example, by embossing or thermoforming or injection molding of the cover sheet.

In certain embodiments, the support sheet is transparent to visible and/or ultraviolet light. This provides an attractive visual appearance, and also means that the certain hydrogels can be cured using visible and/or UV radiation through the support sheet.

Ingredients of the Hydrogel Composition

The preferred hydrogel composition used in the present invention comprises a plasticised three-dimensional matrix of cross-linked polymer molecules, and has sufficient structural integrity to be self-supporting even at very high levels of internal water content, with sufficient flexibility to conform to the surface contours of the human skin. The hydrogel composition preferably has sufficient bioadhesion to adhere to the skin under all skin and moisture conditions likely to be encountered during use. PCT Patent Application No. WO-00/45864, the disclosure of which is incorporated herein by reference, describes a method whereby the skin adhesion performance of the hydrogel can be predicted and thereby tailored to particular applications.

The hydrogel compositions with which the present invention is concerned generally comprise, in addition to the cross-linked polymeric network, an aqueous plasticising medium. The materials and processing methods used are normally chosen to provide suitable adhesive properties for the desired application.

Ionic Monomers

The one or more ionic monomer, if present, will be water soluble and may be selected from: 2-acrylamido-2-methyl-propane sulphonic acid or an analogue thereof or one of its salts (e.g. an ammonium or alkali metal salt such as a sodium, potassium or lithium salts); acrylic acid or an analogue thereof or one of its salts (e.g. an alkali metal salt such as a sodium, potassium or lithium salt); and/or a polymerisable sulphonate or a salt thereof (e.g. an alkali metal salt such as a sodium, potassium or lithium salt), more particularly acrylic acid (3-sulphopropyl) ester or an analogue thereof, or a salt thereof. The term "analogue" in this context refers particularly to substituted derivatives of 2-acrylamido-2-methylpropane sulphonic acid, of acrylic acid or of acrylic acid (3-sulphopropyl) ester.

A further category of ionic monomer that may be mentioned is a monomer/comonomer pair consisting of a first monomer comprising one or more pendant anionic group and a second monomer comprising one or more pendant cationic group, the relative amounts of the said monomers in the pair being such that the anionic groups and cationic groups are present in essentially equimolar quantities. The said anionic and cationic groups may be selected from groups which are salts of acid groups and groups which are salts of basic groups. The pendant groups in the first monomer are preferably the sodium, potassium, calcium, lithium and/or ammonium (individually or in any combination of one or more) salts of carboxylic acid, phosphoric acid and/or sulphonic acid. Sulphonic acid groups are most preferred. The pendant groups in the second monomer are preferably quaternary ammonium salts of halide (for example chloride), sulphate and/or hydroxide. Chloride and sulphate are most preferred.

A particularly preferred ionic monomer is a sodium salt of 2-acrylamido-2-methylpropane sulphonic acid, commonly known as NaAMPS, which is available commercially at present from Lubrizol as either a 50% aqueous solution (reference code LZ2405) or a 58% aqueous solution (reference code LZ2405A) and/or acrylic acid (3-sulphopropyl) ester potassium salt, commonly known as SPA or SPAK. SPA or SPAK is available commercially in the form of a pure solid from Raschig.

Non-Ionic Monomers

The one or more non-ionic monomer, if present, may preferably be water soluble and be selected from acrylamide or a mono- or di-N-alkylacrylamide or an analogue thereof. The term "analogue" in this in this context refers to non-ionic water soluble monomers containing an alkyl or substituted alkyl group linked to a carbon-carbon double bond via an amido or alkylamido (—CO.NH— or —CO.NR—) function. Examples of such analogues include diacetone acrylamide (N-1,1-dimethyl-3-oxobutyl-acrylamide), vinyl lactams, N-alkylated acrylamides, N,N-dialkylated acrylamides, N-vinyl pyrrolidone, N-acryloyl morpholine and any mixture thereof, particularly N-acryloyl morpholine.

Cross-Linking Agents

Conventional cross-linking agents are suitably used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

The one or more organic plasticiser, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plasticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. Non-ionic, anionic and cationic surfactants are preferred. The surfactant ideally comprises any of the surfactants listed below either alone or in combination with each other and/or with other surfactants. The total amount of surfactant, if present, is suitably up to about 10% by weight of the hydrogel composition, preferably from about 0.05% to about 4% by weight.

1. Non-Ionic Surfactants

Suitable non-ionic surfactants include, but are not limited to, those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles and most preferably about 5 to about 20 moles of ethylene oxide. Examples of such non-ionic ethoxylated fatty alcohol surfactants are the Tergitol™ 15-S series from Union Carbide and Brij™ surfactants from ICI. Tergitol™ 15-S surfactants include $C_{11}$-$C_{15}$ secondary alcohol polyethyleneglycol ethers. Brij™ 58 surfactant is polyoxyethylene(20) cetyl ether, and Brij™ 76 surfactant is polyoxyethylene(10) stearyl ether.

Other suitable non-ionic surfactants include, but are not limited to, those selected from the group consisting of the polyethylene oxide condensates of one mole of alkyl phenol containing from about 6 to 12 carbon atoms in a straight or branched chain configuration, with about 3 to about 100 moles of ethylene oxide. Examples of non-ionic surfactants are the Igepal™ CO and CA series from Rhone-Poulenc. Igepal™ CO surfactants include nonylphenoxy poly(ethyleneoxy) ethanols. Igepal™ CA surfactants include octylphenoxy poly(ethyloneoxy) ethanols.

Another group of usable non-ionic surfactants include, but are not limited to, those selected from the group consisting of block copolymers of ethylene oxide and propylene oxide or butylene oxide. Examples of such non-ionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. The balance of hydrophobic and hydrophilic components within the surfactant together with the molecular weight are found to be important. Suitable examples are Pluronic L68 and Tetronic 1907. Particularly suitable examples are Pluronic L64 and Tetronic 1107.

Still other satisfactory non-ionic surfactants include, but are not limited to, those selected from the group consisting of sorbitan fatty acid esters, polyoxyethylene sorbitan fatty acid esters and polyoxyethylene stearates. Examples of such fatty acid ester non-ionic surfactants are the Span™, Tween™, and Myrj™ surfactants from ICI. Span™ surfactants include $C_{12}$-$C_{18}$ sorbitan monoesters. Tween™ surfactants include poly (ethylene oxide) $C_{12}$-$C_{18}$ sorbitan monoesters. Myrj™ surfactants include poly(ethylene oxide) stearates.

2. Anionic Surfactants

Anionic surfactants normally include a hydrophobic moiety selected from the group consisting of (about $C_6$ to about $C_{20}$) alkyl, alkylaryl, and alkenyl groups and an anionic group selected from the group consisting of sulfate, sulfonate, phosphate, polyoxyethylene sulfate, polyoxyethylene sulfonate, polyoxyethylene phosphate and the alkali metal salts, ammonium salts, and tertiary amino salts of such anionic groups.

Anionic surfactants which can be used in the present invention include, but are not limited to those selected from the group consisting of (about $C_6$ to about $C_{20}$) alkyl or alkylaryl sulfates or sulfonates such as sodium lauryl sulfate (commercially available as Polystep™ B-3 from Srepan Co.) and sodium dodecyl benzene sulfonate, (commercially available as Siponate™ DS-10 from Rhone-Poulenc); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep™ B-1 commercially available from Stepan Co. and Alipal™ EP110 and 115 from Rhone-Poulenc; (about $C_6$ to about $C_{20}$) alkyl or alkylphenoxy poly (ethyleneoxy)ethyl mono-esters and di-esters of phosphoric acid and its salts, with the ethylene oxide repeating unit in the surfactant below about 30 units, preferably below about 20 units, most preferably below about 15 units, such as Gafac™ RE-510 and Gafac™ RE-610 from GAF.

3. Cationic Surfactants

Cationic surfactants useful in the hydrogel compositions of the present invention include, but are not limited to, those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl.

In a preferred embodiment of the invention the surfactant comprises at least one propylene oxide/ethylene oxide block copolymer, for example such as that supplied by BASF Plc under the trade name Pluronic P65 or L64.

Other Additives

The hydrogel composition used in the present invention may include one or more additional ingredients, which may be added to the pre-polymerisation mixture or the polymerised product, at the choice of the skilled worker. Such additional ingredients are selected from additives known in the art, including, for example, water, organic plasticisers, surfactants, polymers, pH regulators, colorants, bioactive compounds, personal and body care agents, and mixtures thereof. The polymers can be natural polymers (e.g. xanthan gum), synthetic polymers (e.g. polyoxypropylene-polyoxyethylene block copolymer or poly-(methyl vinyl ether alt maleic anhydride)), or any combination thereof. By "bioactive compounds" we mean any compound or mixture included within the hydrogel for some effect it has on living systems as opposed to the hydrogel, whether the living system be bacteria or other microorganisms or higher animals such as the intended user of articles incorporating the hydrogel. A biocidal biaoactive compound that may particularly be mentioned is citric acid.

Additional polymer(s), typically rheology modifying polymer(s), may be incorporated into the polymerisation reaction mixture at levels typically up to about 10% by weight of total polymerisation reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

Additional functional ingredients may also incorporated in the hydrogel reaction mixture, including bioactive compounds such as antimicrobial agents (e.g. citric acid, stannous chloride), enzymes, compounds providing a heating or cooling sensation to a patient's body, dermatologically active compounds and, for drug delivery applications, pharmaceutically active agents, the latter being designed to be delivered either passively (e.g. transdermally) or actively (e.g. iontophoretically) through the skin.

For use in wound dressings adapted for the delivery of pharmaceuticals or other active agents to or through mammalian skin, the compositions may optionally contain topical, transdermal or iontophoretic agents and excipients. The compositions may contain penetration-enhancing agents to assist the delivery of water or active agents into the skin. Non-limiting examples of penetration-enhancing agents for use in such applications include methyl oleic acid, isopropyl myristate, Azone™, Transcutol™ and N-methyl pyrrolidone.

The additional ingredient may comprise an antimicrobial agent stable against light and radiation, comprising an effective amount of antimicrobial metal (e.g. silver) ions and stabilizing halide (e.g. chloride) ions, wherein the halide is present in an excess (preferably in a substantial molar excess such as around 500-fold excess) with respect to the amount of metal ions.

The hydrogel composition used in the present invention preferably consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, bioactive compounds and mixtures thereof, with less than about 10% by weight of other additives.

Other Components of the Wound Dressing

As already noted, the hydrogel composition is usually used in sheet form as or in the wound dressing. The area of the hydrogel composition sheet in the wound dressing is typically in the range of from 1 cm² to 200 cm², more preferably from 4 cm² to 100 cm². Other configurations of the hydrogel composition besides sheet form can be envisaged for special wound dressing applications, such as filling cavity wounds.

Preferably, the wound dressing comprises an absorbent layer and/or a backing layer in addition to the layer of the hydrogel composition, in which case the hydrogel composition is preferably the wound-facing top sheet of the dressing.

Preferably, the dressing further comprises a backing layer over the back face (i.e preferably over the first portion) of the hydrogel composition. The backing layer preferably provides a barrier to passage of microorganisms through the dressing and further preferably blocks the escape of wound fluid from the dressing. The backing layer may extend beyond at least one edge of the hydrogel composition layer to provide an adhesive-coated margin adjacent to the said edge for adhering the dressing to a surface, such as to the skin of a patient adjacent to the wound being treated. An adhesive-coated margin may extend around all sides of the hydrogel composition layer, so that the dressing is a so-called island dressing. However, it is not necessary for there to be any adhesive-coated margin.

Preferably, the backing layer is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 $g/m^2/24$ hrs, preferably 500 to 2000 $g/m^2/24$ hrs at 37.5° C. at 100% to 10% relative humidity difference. The backing sheet thickness is preferably in the range of 10 to 1000 micrometers, more preferably 100 to 500 micrometers.

The MVTR of the dressing according to the present invention as a whole is lower than that of the backing sheet alone, because the hydrogel composition partially obstructs moisture transfer through the dressing. Preferably, the MVTR of the dressing (measured across the island portion of the dressing) is from 20% to 80% of the MVTR of the backing sheet alone, more preferably from 20% to 60% thereof, and most preferably about 40% thereof. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type, conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 $g/m^2$, and more preferably 50 to 150 $g/m^2$. Polyurethane-based pressure sensitive adhesives are preferred.

In certain embodiments, the dressing further comprises a further, optional absorbent layer intermediate the back face (i.e the first portion) of the hydrogel composition and the backing sheet. The area of the optional absorbent layer is typically in the range of from 1 $cm^2$ to 200 $cm^2$, more preferably from 4 $cm^2$ to 100 $cm^2$. In certain embodiments the optional absorbent layer is coextensive with the hydrogel composition layer.

The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 $g/m^2$, such as 100-400 $g/m^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°

The wound dressing according to the present invention preferably further comprises at least one removable cover sheet covering the wound facing surface of the hydrogel composition sheet and any adhesive coated margin of the backing sheet around the hydrogel. The cover sheet covers and protects the hydrogel and prevents premature adhesion of the adhesive layer. The cover sheet is removed by the care giver immediately before application of the dressing.

The cover sheet may comprise a film of polyethylene, polypropylene or fluorocarbons and papers coated with these materials.

In certain embodiments, the cover sheet is the support sheet used to cast the hydrogel composition layer, as discussed above. In other embodiments, the cover sheet is applied to the hydrogel layer after it has been made. In these embodiments, the cover sheet may be a release-coated paper sheet, such as a silicone release-coated paper sheet. Examples of silicone-coated release papers are POLYSLIK (Registered Trade Mark) supplied by H.P. Smith & Co., offered in various formulations to control the degree of adhesion of the paper to the adhesive surface.

Certain preferred dressings have a central cover sheet with first and second opposed edges, and two side cover sheets that meet the central cover sheet along the opposed edges. Preferably, the opposed edges are substantially parallel. This arrangement of three cover sheets is especially suitable for positioning of relatively large dressings, such as sacral dressings, as described in detail in EP-A-0117632, the entire content of which is incorporated herein by reference. Preferably, along each of said edges where the cover sheets meet, one of the cover sheets is folded back to provide a folded-back margin, and the other cover sheet overlaps the said folded-back margin. This provides an easy-to-grasp margin on each cover sheet in the region of overlap to assist removal of the cover sheets by the care giver. In the case of the embodiment comprising three cover sheets described above, each side cover sheet is preferably folded back along each of said edges where the cover sheets meet to provide a folded-back margin, and the central cover sheet overlaps the said folded-back margin, preferably as described in EP-A-0117632.

Preferably, the wound dressing according to the present invention is sterile and packaged in a microorganism-impermeable container.

EXAMPLES

The invention will be further described with reference to the following Examples, which should not be understood to limit the scope of the invention.

Test Methods

Pre-foam viscosity was determined using a Brookfield Viscometer with a S18 spindle in a closed volume at a speed of 20 rpm. The pre-cured foam viscosities were also determined using a Brookfield Viscometer with a S18 spindle in a closed volume at a speed of 2 rpm.

The rate of absorption of water on the continuous layer and on the porous layer were determined by placing a 5 μl drop from a syringe and monitoring the drop volume on the surface of the material over the first 0.1 s. This was done using a Scientific and Medical Products DAT1100 dynamic contact angle analyser.

The rheology of the hydrogel foam composite was determined with a Rheometrics SR5 rheometer over a range from 0.1 to 100 rad/s.

Water activities of the foamed hydrogels were determined with an AquaLab Series 3TE water activity meter.

Preparative Methods and Compositions

Preparative Method and Apparatus

The method for making 200 g of hydrogel foam will be described below. It will be appreciated by those skilled in the art that this may be scaled up to enable semi-continuous or continuous hydrogel foam to be made.

200 g of hydrogel pre-foam formulation mix is added to a 500 ml vessel. A paddle stirrer is placed into the pre-foam formulation mix. The paddle is connected to an IKA RW 16 Basic mixer. The mix is stirred for three minutes at a speed of 500 to 600 rpm until the mix is frothy and has increased in viscosity. It will be appreciated that different mixing times and speeds may be employed depending on the extent of foaming required. At the end of the foaming period the paddle is removed from the vessel. The foam is then poured (cast), to a depth of about 5 to 6 mm, onto a polyethylene film release layer having a grid array of upwardly extending tapered projections consisting of embossed nipples in the film approximately 2 to 3 mm high extending from its upper surface, and irradiated with UV light (for example from a medium pressure mercury arc lamp) to cure the foam. The resulting material is according to this invention a composite structure comprising a continuous hydrogel layer provided with apertures therethrough (corresponding to the nipples in shape and location) in contact with the polyethylene release layer and a porous layer adjacent to it. By casting the foamed mix onto a moving substrate, a continuous roll of composite material can be produced at speeds from 0.5 m/min to 30 m/min. Variation of the extent of foaming and the time between casting the foam and then curing allows the thickness ratio of the continuous and porous layer portions of the hydrogel sheet to be altered and controlled.

Examples 1 to 15

Compositions

The compositions of the hydrogels prepared are shown below:

| | | Example Number | |
|---|---|---|---|
| | | 1 | 2 |
| N-Acryloylmorpholine | % | 0.0 | 0.0 |
| Sodium 2-acrylamido-2-methylpropane sulphonate | % | 31.3 | 56.8 |
| N,N-Dimethylaminoethylacrylate, methyl chloride quarternary salt | % | 26.2 | 0.0 |
| N,N-Dimethylacrylamide | % | 0.0 | 0.0 |
| 3-Sulphopropyl acrylate potassium salt | % | 0.0 | 0.0 |
| Acrylic Acid | % | 0.0 | 0.0 |
| Sodium Acrylate | % | 0.0 | 0.0 |
| Glycerol | % | 9.9 | 0.0 |
| Water | % | 29.6 | 41.2 |
| Citric Acid | % | 0.0 | 0.0 |
| Silver Nitrate | % | 0.0 | 0.0 |
| Magnesium Chloride hexahydrate | % | 0.0 | 0.0 |
| Polyoxypropylene-Polyoxyethylene block co-polymer | % | 3.0 | 2.0 |
| Daracure 1173/Irgacure 280 15/20 | g/100 g | 0.0 | 0.0 |
| Daracure 1173/Irgacure 280 8/20 | g/100 g | 0.0 | 0.0 |
| Daracure 1173/Irgacure 280 6/20 | g/100 g | 0.0 | 0.0 |
| Daracure 1173/Irgacure 280 4/20 | g/100 g | 0.7 | 0.0 |
| Daracure 1173/Irgacure 280 1/20 | g/100 g | 0.0 | 0.6 |

| | | Example Number | |
|---|---|---|---|
| | | 3 | 4 |
| N-Acryloylmorpholine | % | 48.4 | 48.0 |
| Sodium 2-acrylamido-2-methylpropane sulphonate | % | 1.9 | 1.9 |
| N,N-Dimethylaminoethylacrylate, methyl chloride quarternary salt | % | 0.0 | 0.0 |
| N,N-Dimethylacrylamide | % | 0.0 | 0.0 |
| 3-Sulphopropyl acrylate potassium salt | % | 0.0 | 0.0 |
| Acrylic Acid | % | 0.0 | 0.0 |
| Sodium Acrylate | % | 0.0 | 0.0 |
| Glycerol | % | 32.3 | 32.0 |
| Water | % | 14.3 | 14.1 |
| Citric Acid | % | 0.0 | 0.8 |
| Silver Nitrate | % | 0.0 | 0.0 |
| Magnesium Chloride hexahydrate | % | 0.0 | 0.0 |
| Polyoxypropylene-Polyoxyethylene block co-polymer | % | 3.2 | 3.2 |
| Daracure 1173/Irgacure 280 15/20 | g/100 g | 0.0 | 0.0 |
| Daracure 1173/Irgacure 280 8/20 | g/100 g | 0.0 | 0.0 |
| Daracure 1173/Irgacure 280 6/20 | g/100 g | 1.2 | 1.2 |
| Daracure 1173/Irgacure 280 4/20 | g/100 g | 0.0 | 0.0 |
| Daracure 1173/Irgacure 280 1/20 | g/100 g | 0.0 | 0.0 |

| | | Example Number | |
|---|---|---|---|
| | | 5 | 6 |
| N-Acryloylmorpholine | % | 28.4 | 48.7 |
| Sodium 2-acrylamido-2-methylpropane sulphonate | % | 0 | 5.7 |
| N,N-Dimethylaminoethylacrylate, methyl chloride quarternary salt | % | 0 | 0 |
| N,N-Dimethylacrylamide | % | 0.0 | 0 |
| 3-Sulphopropyl acrylate potassium salt | % | 0.0 | 0 |
| Acrylic Acid | % | 0.0 | 0 |
| Sodium Acrylate | % | 0.0 | 0 |
| Glycerol | % | 14.3 | 39 |
| Water | % | 18.9 | 4.1 |
| Citric Acid | % | 0 | 0 |
| Silver Nitrate | % | 0.0 | 0 |
| Magnesium Chloride hexahydrate | % | 36 | 0 |
| Polyoxypropylene-Polyoxyethylene block co-polymer | % | 2.4 | 2.4 |
| Daracure 1173/Irgacure 280 15/20 | g/100 g | 0.0 | 0.4 |
| Daracure 1173/Irgacure 280 8/20 | g/100 g | 0.1 | 0.0 |
| Daracure 1173/Irgacure 280 6/20 | g/100 g | 0.0 | 0.0 |
| Daracure 1173/Irgacure 280 4/20 | g/100 g | 0.0 | 0.0 |
| Daracure 1173/Irgacure 280 1/20 | g/100 g | 0.0 | 0.0 |

| | | Example Number | |
|---|---|---|---|
| | | 7 | 8 |
| N-Acryloylmorpholine | % | 0.0 | 0.0 |
| Sodium 2-acrylamido-2-methylpropane sulphonate | % | 7.6 | 0.0 |
| N,N-Dimethylaminoethylacrylate, methyl chloride quarternary salt | % | 0.0 | 0.0 |
| N,N-Dimethylacrylamide | % | 0.0 | 0.0 |
| 3-Sulphopropyl acrylate potassium salt | % | 0.0 | 0.0 |
| Acrylic Acid | % | 0.0 | 0.0 |
| Sodium Acrylate | % | 25.1 | 28.5 |
| Glycerol | % | 0.0 | 0.0 |
| Water | % | 64.1 | 66.8 |
| Citric Acid | % | 0.0 | 0.0 |
| Silver Nitrate | % | 0.0 | 0.0 |
| Magnesium Chloride hexahydrate | % | 0.0 | 0.0 |
| Polyoxypropylene-Polyoxyethylene block co-polymer | % | 3.3 | 0.0 |
| Daracure 1173/Irgacure 280 15/20 | g/100 g | 0.0 | 0.0 |

-continued

| | | | |
|---|---|---|---|
| Daracure 1173/Irgacure 280 8/20 | g/100 g | 0.0 | 0.0 |
| Daracure 1173/Irgacure 280 6/20 | g/100 g | 0.0 | 0.0 |
| Daracure 1173/Irgacure 280 4/20 | g/100 g | 0.0 | 0.0 |
| Daracure 1173/Irgacure 280 1/20 | g/100 g | 0.8 | 0.7 |

| | | Example Number | |
|---|---|---|---|
| | | 9 | 10 |
| N-Acryloylmorpholine | % | 0.00 | 0.0 |
| Sodium 2-acrylamido-2-methylpropane sulphonate | % | 56.77 | 32.8 |
| N,N-Dimethylaminoethylacrylate, methyl chloride quarternary salt | % | 0.00 | 0.0 |
| N,N-Dimethylacrylamide | % | 0.00 | 0.0 |
| 3-Sulphopropyl acrylate potassium salt | % | 0.00 | 9.6 |
| Acrylic Acid | % | 0.00 | 1.9 |
| Sodium Acrylate | % | 0.00 | 0.0 |
| Glycerol | % | 0.00 | 33.7 |
| Water | % | 41.11 | 23.0 |
| Citric Acid | % | 0.00 | 0.0 |
| Silver Nitrate | % | 0.01 | 0.0 |
| Magnesium Chloride hexahydrate | % | 0.00 | 0.0 |
| Polyoxypropylene-Polyoxyethylene block co-polymer | % | 2.11 | 1.9 |
| Daracure 1173/Irgacure 280 15/20 | g/100 g | 0.00 | 0.0 |
| Daracure 1173/Irgacure 280 8/20 | g/100 g | 0.00 | 0.0 |
| Daracure 1173/Irgacure 280 6/20 | g/100 g | 0.00 | 0.0 |
| Daracure 1173/Irgacure 280 4/20 | g/100 g | 0.00 | 0.0 |
| Daracure 1173/Irgacure 280 1/20 | g/100 g | 0.7 | 0.1 |

| | | Example Number | |
|---|---|---|---|
| | | 11 | 12 |
| N-Acryloylmorpholine | % | 0.0 | 0.0 |
| Sodium 2-acrylamido-2-methylpropane sulphonate | % | 0 | 0 |
| N,N-Dimethylaminoethylacrylate, methyl chloride quarternary salt | % | 0.0 | 0.0 |
| N,N-Dimethylacrylamide | % | 47.5 | 0.0 |
| 3-Sulphopropyl acrylate potassium salt | % | 0.0 | 49.0 |
| Acrylic Acid | % | 0.0 | 0.0 |
| Sodium Acrylate | % | 0.0 | 0.0 |
| Glycerol | % | 40.0 | 24.2 |
| Water | % | 10.0 | 24.3 |
| Citric Acid | % | 0.0 | 0.0 |
| Silver Nitrate | % | 0.0 | 0.0 |
| Magnesium Chloride hexahydrate | % | 0.0 | 0.0 |
| Polyoxypropylene-Polyoxyethylene block co-polymer | % | 2.5 | 2.5 |
| Daracure 1173/Irgacure 280 15/20 | g/100 g | 0.0 | 0.0 |
| Daracure 1173/Irgacure 280 8/20 | g/100 g | 0.0 | 0.0 |
| Daracure 1173/Irgacure 280 6/20 | g/100 g | 0.7 | 0.0 |
| Daracure 1173/Irgacure 280 4/20 | g/100 g | 0.0 | 0.3 |
| Daracure 1173/Irgacure 280 1/20 | g/100 g | 0.0 | 0.0 |

| | | Example Number |
|---|---|---|
| | | 13 |
| N-Acryloylmorpholine | % | 0.0 |
| Sodium 2-acrylamido-2-methylpropane sulphonate | % | 0 |
| N,N-Dimethylaminoethylacrylate, methyl chloride quarternary salt | % | 28.2 |
| NN Dimethylacrylamide | % | 0.0 |
| 3-Sulphopropyl acrylate potassium salt | % | 0 |
| Acrylic Acid | % | 0.0 |
| Sodium Acrylate | % | 0.0 |
| Glycerol | % | 47.3 |
| Water | % | 18.9 |
| Citric Acid | % | 0.0 |
| Silver Nitrate | % | 0.0 |
| Magnesium Chloride hexahydrate | % | 0.0 |
| Polyoxypropylene-Polyoxyethylene block co-polymer | % | 5.5 |
| Daracure 1173/Irgacure 280 15/20 | g/100 g | 0.0 |
| Daracure 1173/Irgacure 280 8/20 | g/100 g | 0.9 |
| Daracure 1173/Irgacure 280 6/20 | g/100 g | 0.0 |
| Daracure 1173/Irgacure 280 4/20 | g/100 g | 0.0 |
| Daracure 1173/Irgacure 280 1/20 | g/100 g | 0.0 |

Compositions Containing Thickeners and or Fillers

| | | Example Number | |
|---|---|---|---|
| | | 14 | 15 |
| N-Acryloylmorpholine | % | 0.0 | 0.0 |
| Sodium 2-acrylamido-2-methylpropane sulphonate | % | 31.3 | 34.6 |
| N,N-Dimethylaminoethylacrylate, methyl chloride quarternary salt | % | 26.2 | 28.9 |
| Glycerol | % | 0.0 | 0.0 |
| Water | % | 38.5 | 32.7 |
| Poly (methyl vinyl ether alt maleic anhydride) | % | 1.0 | 0.0 |
| Xanthan gum | % | 0.0 | 0.5 |
| Polyoxypropylene-Polyoxyethylene block co-polymer | % | 3.0 | 3.3 |
| Daracure 1173/Irgacure 280 15/20 | g/100 g | 0.0 | 0.0 |
| Daracure 1173/Irgacure 280 8/20 | g/100 g | 0.0 | 0.0 |
| Daracure 1173/Irgacure 280 6/20 | g/100 g | 0.7 | 0.7 |
| Daracure 1173/Irgacure 280 4/20 | g/100 g | 0.0 | 0.0 |
| Daracure 1173/Irgacure 280 1/20 | g/100 g | 0.0 | 0.0 |

Test Results and Discussion

Certain physical parameters of the compositions prepared in Examples 1 to 6 were tested using the test methods described above. The results are shown below (Aw=water activity):

| Example | Pre-Foam Viscosity (mPas) | Foam Pre-Cure Viscosity (mPas) | Cured Foam Water Absorption Continuous Layer (microl/s) | Cured Foam Water Absorption Porous Layer (microl/s) |
|---|---|---|---|---|
| 1 | 33 | 324 | 0 | 5 |
| 2 | 28 | 878 | 0.1 | 4 |
| 3 | 40 | 640 | 0 | 25 |
| 4 | 29 | 465 | 5 | 13 |
| 5 | Na | Na | 1 | 4 |
| 6 | Na | Na | 0 | 3 |

| Example | Cured Foam Elastic modulus @ 1 (rad/s) (Pa) | Cured Foam Elastic Modulus @ 100 (rad/s) (Pa) | Cured Foam Viscous Modulus @ 1 (rad/s) (Pa) | Aw |
|---|---|---|---|---|
| 1 | 8887 | 13730 | 1487 | 0.74 |
| 2 | 8197 | 16666 | 2636 | 0.78 |
| 3 | 1688 | 3305 | 467 | 0.48 |
| 4 | 1567 | 3714 | 535 | 0.48 |
| 5 | 5062 | 10386 | 1383 | 0.46 |
| 6 | 14479 | 99239 | 9698 | 0.27 |

In all of Examples 1 to 15, the foamed hydrogels produced were acceptable gels having good to excellent water uptake rate on the porous side. In the Examples tested (Examples 1 to 6), the foamed hydrogels had acceptable water activity, elastic and viscous moduli for use in the applications described above.

INDUSTRIAL APPLICABILITY

The present invention makes available wound dressings comprising porous hydrogels with useful capacity to absorb potentially large quantities of liquids at an acceptable speed for many uses. Moreover, the hydrogels can be made conveniently and efficiently, preferably under a process in which polymerisation of the pre-gel mixture is substantially the final processing step in the hydrogel manufacture, with no or only very trivial post-processing of the hydrogel being required.

The present invention has been broadly described without limitation. Variations and modifications as will be readily apparent to those skilled in the art are intended to be covered by the present application and resultant patents.

The invention claimed is:

1. A wound dressing comprising a hydrogel composition, said hydrogel composition comprising a first portion which comprises a flexible plasticized hydrophilic polymer matrix having an internal cellular structure, and a second portion which comprises a flexible plasticized hydrophilic polymer matrix having a relatively continuous internal structure, wherein the first and the second portion are of the same material, wherein an outward facing surface of the second portion is a skin-contactable surface, wherein the second portion of the hydrogel composition includes apertures providing fluid flow communication through the second portion between the skin-contactable surface of the second portion and the first portion, and wherein the apertures of the second portion of the hydrogel composition continue into the first portion of the composition to invade it, without penetrating it entirely, whereby the first portion and second portion of the hydrogel composition can take up external water or other fluid into the cellular structure through the apertures of the second portion and first portion.

2. A wound dressing according to claim 1, wherein the dressing further comprises a backing layer over the hydrogel composition.

3. A wound dressing according to claim 2, wherein the backing layer is substantially liquid-impermeable.

4. A wound dressing according to claim 3, further comprising a layer of adhesive on the surface of the backing layer facing the hydrogel composition.

5. A wound dressing according to claim 4, wherein the backing layer extends beyond at least one edge of the layer of hydrogel composition to provide an adhesive-coated margin adjacent to said edge for adhering the dressing to a surface.

6. A wound dressing according to claim 5, further comprising at least one removable cover sheet to cover the wound facing surface of the hydrogel composition before use.

7. A wound dressing according to claim 6, wherein the removable cover sheet provided with projections which extend into the apertures in the hydrogel composition.

8. A wound dressing according to claim 7, wherein the projections extend only part way into the hydrogel sheet.

9. A wound dressing according to claim 1, further comprising an absorbent layer for receiving fluid transmitted through said hydrogel composition.

10. A wound dressing according to claim 9, wherein the absorbent layer comprises a further layer of hydrophilic foam.

11. A wound dressing according to claim 6, which is sterile and packaged in a microorganism-impermeable container.

12. A wound dressing according to claim 1, wherein the first portion of said hydrogel composition comprises a porous foam having an internal cellular structure such that the volume ratio of cell void to matrix is greater than about 1:3 and the second portion comprises a relatively non-porous matrix.

13. A wound dressing according to claim 1, wherein one or both of the said portions of the hydrogel composition is adhered to the skin.

14. A wound dressing according to claim 1, wherein the external surface of the said second portion of the hydrogel composition defines a wound contacting surface of the dressing.

15. A wound dressing according to claim 1, wherein the absorption capacity of the hydrogel composition is between about 30% and about 10000%.

16. A wound dressing according to claim 1, wherein the water uptake rate of the first portion of the hydrogel composition is at least about 2 µl/s as measured by the test method described herein.

17. A wound dressing according to claim 1 in the form of a sheet, wherein the sheet has a substantially uniform thickness of between about 0.5 to about 10 mm.

18. A wound dressing according to claim 1, wherein the hydrogel composition has been obtained by a process which comprises polymerising a polymerisable mixture comprising a hydrophilic monomer, where the polymerisable mixture prior to polymerization comprises a first portion including a relatively high concentration of introduced gas bubbles and a second portion including a relatively low concentration of gas bubbles.

19. The wound dressing of claim 1, wherein the apertures have a tapered shape with the wide end of the tapered shape at the skin contacting surface.

20. A method for dressing a wound or a burn, comprising covering the wound or burn with a dressing comprising a hydrogel composition comprising a first portion which comprises a flexible plasticized hydrophilic polymer matrix having an internal cellular structure, and a second portion which comprises a flexible plasticized hydrophilic polymer matrix having relatively continuous internal structure, wherein the first and second portion are of the same material, wherein an outward facing surface of said second portion is a skin-contactable surface, and wherein the said second portion of the hydrogel composition includes apertures providing fluid flow communication through the said second portion between the skin-contactable surface of the said second portion and the first portion, and wherein the apertures of the second portion of the hydrogel composition continue into the first portion of the composition to invade it, without penetrating it entirely, whereby the first and second portion of the hydrogel composition can take up external water or other fluid into the cellular structure through the apertures of the said first and second portion.

21. The wound dressing of claim 19, wherein the apertures have a dimension at the skin contact surface of from 1 mm to 3 mm and a width at the top of the second hydrogen composition of 0.1 to 1 mm.

22. The wound dressing of claim 19, wherein the angle of taper, measured from the perpendicular to the plane of the support sheet, is from 10 to 60 degrees.

23. The wound dressing of claim 19, wherein the mean cross-sectional area of the apertures at their mid-point is from 10 to 25% of the total area of the central region of the first hydrophilic polymer.

24. The wound dressing of claim 19, wherein the density of the apertures is from 10 to 100 per $cm^2$.

25. The method for dressing a wound or a burn of claim 20, wherein the apertures have a tapered shape with the wide end of the tapered shape at the skin contacting surface.

* * * * *